United States Patent [19]

Katsura et al.

[11] Patent Number: 5,621,134
[45] Date of Patent: Apr. 15, 1997

[54] METHOD FOR PRODUCING 4'-BROMOMETHYL-2-CYANOBIPHENYL

[75] Inventors: Tadashi Katsura, Toyonaka; Hiroshi Shiratani, Osaka, both of Japan

[73] Assignee: Sumika Fine Chemicals Co., Ltd., Osaka, Japan

[21] Appl. No.: 543,948

[22] Filed: Oct. 17, 1995

[30] Foreign Application Priority Data

Oct. 27, 1994 [JP] Japan .................................. 6-289079

[51] Int. Cl.⁶ ................................................ C07C 253/30
[52] U.S. Cl. ................................................ 558/388
[58] Field of Search ............................................ 558/388

[56] References Cited

U.S. PATENT DOCUMENTS 4,087,473  5/1978  Markley .

FOREIGN PATENT DOCUMENTS 0052744  6/1982  European Pat. Off. .
0553879  8/1993  European Pat. Off. .

OTHER PUBLICATIONS

Chemical Abstract No. 119:203113n (Aug. 4, 1993).
Chemical Abstract No. 109:129008g (Jan. 20, 1988).
Chemical Abstract No. 122:132735 (Oct. 25, 1994).
Chemical Abstract No. 122:132734 Oct. 25, 1994).
Carini et al, J. Med. Chem., vol. 34, pp. 2525–2547 (1991).

*Primary Examiner*—Johann Richter
*Assistant Examiner*—John Peabody
*Attorney, Agent, or Firm*—Birch, Stewart, Kolasch & Birch, LLP

[57] ABSTRACT

A method for producing 4'-bromomethyl-2-cyanobiphenyl by the step of treating 4'-methyl-2-cyanobiphenyl with $Br_2$ in a halogenated hydrocarbon solvent or an alkane solvent having 5 to 7 carbon atoms.

6 Claims, No Drawings

METHOD FOR PRODUCING 4'-BROMOMETHYL-2-CYANOBIPHENYL

FIELD OF THE INVENTION

The present invention relates to a method for producing 4'-bromomethyl-2-cyanobiphenyl useful as synthetic intermediates for medicinal purposes industrially advantageously.

BACKGROUND OF THE RELATED ART

Japanese Patent Laid-Open No. 63-23868 discloses biphenylmethylimidazole compounds which have an antagonistic action to angiotensin II and are useful as antihypertensives and therapeutic medicines for congestive cardiac incompetence. The publication discloses that a 4-bromomethylbiphenyl compound used as a synthetic intermediate for the biphenylmethylimidazole compounds is produced by bromination of a 4-methylbiphenyl compound with N-bromosuccinimide in a carbon tetrachloride solvent in the presence of dibenzoyl peroxide at a temperature not more than a reflux temperature.

Also, Japanese Patent Laid-Open No. 6-192170 discloses a method of using an azobis compound as a radical initiator while using a bromination agent similar to the above in order to solve the problems in yield and operability.

However, both of these methods have to employ expensive bromination agents such as N-bromosuccinimide. In the latter case where the yield is somewhat improved from the former case, the presence of the dibromo-product, which is formed as a by-product, causes to lower the selectivity of the monobromo-product to 85 or 90%, and the yield to 70 or 80%. Therefore, both methods cannot be considered as industrially advantageous production methods.

SUMMARY OF THE INVENTION

An object of the present invention is to provide a method for producing 4'-bromomethyl-2-cyanobiphenyl industrially advantageously by using industrially inexpensive starting materials at a high yield, thus being industrially advantageous.

As a result of intense investigation in view of achieving the above object, the present inventors have found that by using industrially inexpensive $Br_2$ as a bromination agent, the desired monobromo-product can be produced at a surprisingly high selectivity of from 90 to 95%, and with an increased yield of from 80 to 90%, as compared with from 70 to 80% yield in a conventional method. The present invention have been completed based upon these findings.

The gist of the present invention is as follows:

(1) A method for producing 4'-bromomethyl-2-cyanobiphenyl represented by formula (II):

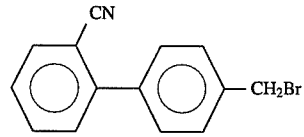

comprising a step of treating 4'-methyl-2-cyanobiphenyl represented by formula (I):

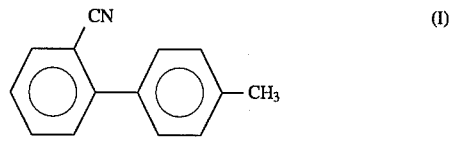

with $Br_2$ in a halogenated hydrocarbon solvent or an alkane solvent having 5 to 7 carbon atoms;

(2) The method described in (1) above, wherein the step is carried out in the presence of a radical initiator;

(3) The method described in (1) above, wherein $Br_2$ is used in an amount of from 0.8 to 1.5 times by mol, based on said 4'-methyl-2-cyanobiphenyl;

(4) The method described in (1) above, wherein the solvent is selected from the group consisting of methylene chloride, ethylene dichloride, carbon tetrachloride, monochlorobenzene, o-dichlorobenzene, bromobenzene, hexane, heptane, and cyclohexane;

(5) The method described in (1) above, wherein an amount of the solvent used is from 1 to 20 times the weight of 4'-methyl-2-cyanobiphenyl;

(6) The method described in (2) above, wherein the radical initiator is selected from the group consisting of 2,2'-azobis(4-methoxy-2,4-dimethylvaleronitrile), 2,2'-azobisisobutyronitrile, and dibenzoyl peroxide;

(7) The method described in (2) above, wherein an amount of the radical initiator used is from 0.1 to 10 mol %, based on 4'-methyl-2-cyanobiphenyl; and (8) The method described in (1) above, wherein a reaction temperature is from 0° to 100° C.

DETAILED DESCRIPTION OF THE INVENTION

The reaction scheme of the method for producing 4'-bromomethyl-2-cyanobiphenyl is as follows:

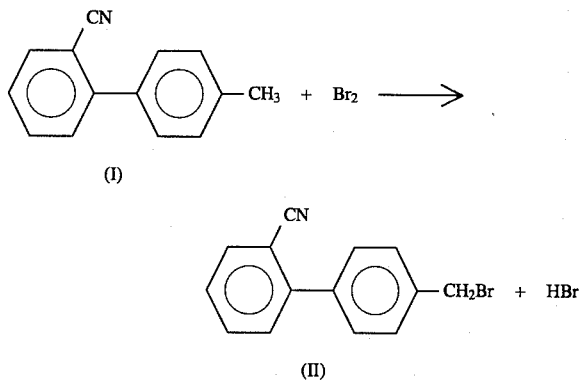

Here, $Br_2$ is used in an amount of from 0.8 to 1.5 times by mol, preferably from 0.9 to 1.2 times by mol, more preferably from 0.95 to 1.05 times by mol, based on 4'-methyl-2-cyanobiphenyl. When the amount of $Br_2$ is less than the lower limit of the above range, the unchanged starting material is likely to remain. On the other hand, when the amount exceeds the upper limit of the above range, the amount of the dibromo-product produced as a by-product is likely to be increased.

4'-Methyl-2-cyanobiphenyl, which is used as the starting material, may be produced by any known methods, such as a method disclosed in J. Med. Chem. 1991, 34, pp.

2525–2547, and methods disclosed in Japanese Patent Laid-Open Nos. 4-244080, 4-253949, and 6-9536.

The solvents which are usable in the above reaction are halogenated hydrocarbons and alkanes having 5 to 7 carbon atoms. Specific examples thereof include methylene chloride, ethylene dichloride, carbon tetrachloride, monochlorobenzene, o-dichlorobenzene, bromobenzene, hexane, heptane, and cyclohexane. Among them, a preference is given to ethylene dichloride and monochlorobenzene.

Incidentally, the reasons why the halogenated hydrocarbons and the alkanes having 5 to 7 carbon atoms are used as solvents in the present invention are that these solvents are less susceptible to bromination reaction than the starting material, thereby suppressing the side reaction.

The amount of the solvents used is from 1 to 20 times the weight of 4'-methyl-2-cyanobiphenyl used as the starting material, preferably from 3 to 15 the weight thereof. When the amount of the solvent is lower than the lower limit of the above range, the reaction rate is liable to slow down, thereby making it industrially disadvantageous.

In the present invention, though not being limited thereto, the reaction may be preferably carried out in the presence of a radical initiator. The radical initiators include azobis compounds and peroxides. Examples thereof include azobis compounds, such as 2,2'-azobis(4-methoxy-2,4-dimethylvaleronitrile), 2,2'-azobisisobutyronitrile, and 2,2'-azobis(2,4,-dimethylvaleronitrile); and peroxides, such as dibenzoyl peroxide and di-t-butyl peroxide, with a preference given to 2,2'-azobis(4-methoxy-2,4-dimethylvaleronitrile), 2,2'-azobisisobutyronitrile, and dibenzoyl peroxide, and particularly 2,2'-azobis(4-methoxy-2,4-dimethylvaleronitrile).

The amount of the radical initiators used is from 0.1 to 10 mol%, preferably from 1 to 6 mol%, based on 4'-methyl-2-cyanobiphenyl used as the starting material. When the amount of the radical initiator is lower than the lower limit of the above range, the reaction rate is liable to slow down, and when the amount of the radical initiator exceeds the upper limit of the above range, no further effects are obtained by addition thereof, thereby making it industrially disadvantageous.

Although the reaction temperature differs depending upon radical initiators and other agents used, it is normally from 0° to 100° C., preferably from 20° to 80° C. When the reaction temperature is lower than the lower limit of the above range, the reaction rate is liable to slow down, and when the reaction temperature exceeds the upper limit of the above range, the radical initiator is liable to be unstable, thereby making it meaningless for industrial purposes. Incidentally, the radical initiators may form radicals by photo irradiation. In such cases, mercury lamp, etc. may be used for photo irradiation Alternatively, simply an application of photo irradiation or heating at a temperature of 100° to 150° C. may be sufficient to cause radical formation without using a radical initiator.

In addition, the reaction time can be suitably chosen depending upon various reaction conditions, for instance, from about 1 to 5 hours.

4'-Bromomethyl-2-cyanobiphenyl thus obtained above can be isolated and purified from the reaction mixture, for instance, by removing the solvent by a conventional method, and then recrystallizing from a suitable separate solvent, without limiting the isolation and purification methods thereto.

In the present invention, by carrying out the above production method, the desired 4'-bromomethyl2-cyanobiphenyl can be obtained at a high selectivity and a high yield.

In addition, 4'-bromomethyl-2-cyanobiphenyl obtainable in the present invention is useful as synthetic intermediates for medicinal purposes.

According to the method of the present invention, 4'-bromomethyl-2-cyanobiphenyl can be industrially advantageously produced at a high yield using inexpensive starting materials in an industrial scale.

EXAMPLES

Example 1

Fifty grams (0.2591 mol) of 4'-methyl-2-cyanobiphenyl, 500 g of ethylene dichloride, and 4.0 g (0.0130 mol) of 2,2'-azobis(4-methoxy-2,4-dimethylvaleronitrile) were placed in a reaction vessel, and the internal temperature was controlled to 40°±2° C. Thereafter, 41.4 g (0.2591 mol) of $Br_2$ was added dropwise at the same temperature over a period of 2 hours, and then the reaction mixture was kept at that temperature for one hour.

At this point of reaction, samples were taken out from the reaction mixture, and they were subjected to LC analysis. As a result, it was found that the mixture contained 2.5% of the starting material, 92.0% of the monobromo-product, and 5.0% of the dibromo-product. Accordingly, the selectivity of the monobromo-product over the dibromo-product was 94.8%.

Thereafter, the reaction mixture was washed with 250 g of water, and then the mixture was separated to two layers. The organic layer was condensed by removing the solvent. The obtained solid was recrystallized from ethylene dichloride (150 ml)-n-heptane (600 ml), to give 63.1 g of 4'-bromomethyl-2-cyanobiphenyl with an LC purity of 99.0%. The yield was 89.4%, based on the starting material.

Example 2

The same procedures as in Example 1 were carried out except that 2.1 g (0.0128 mol) of 2,2'-azobisisobutyronitrile was used in place of 2,2'-azobis(4-methoxy-2,4-dimethylvaleronitrile), and the reaction temperature was changed to 70° C. After completion of the reaction, samples were taken out from the reaction mixture, and they were subjected to LC analysis. As a result, it was found that the mixture contained 3.0% of the starting material, 87.0% of the monobromo-product, and 8.5% of the dibromo-product. Accordingly, the selectivity of the monobromo-product over the dibromo-product was 91.1%.

Thereafter, the purification treatment as in Example 1 was carried out, to give 58.5 g of 4'-bromomethyl-2-cyanobiphenyl with an LC purity of 98.5%. The yield was 83.0%, based on the starting material.

Example 3

The same procedures as in Example 1 were carried out except that 3.1 g (0.0128 mol) of dibenzoyl peroxide was used in place of 2,2'-azobis(4-methoxy-2,4-dimethylvaleronitrile), and the reaction temperature was changed to 80° C. After completion of the reaction, samples were taken out from the reaction mixture, and they were subjected to LC analysis. As a result, it was found that the mixture contained 3.5% of the starting material, 86.0% of the monobromo-product, and 9.5% of the dibromo-product. Accordingly, the selectivity of the monobromo-product over the dibromo-product was 90.1%.

Thereafter, the purification treatment as in Example 1 was carried out, to give 57.5 g of 4'-bromomethyl-2-cyanobiphenyl with an LC purity of 98.0%. The yield was 81.6%, based on the starting material.

Example 4

The same procedures as in Example 1 were carried out except that 500 g of monochlorobenzene was used in place of ethylene dichloride. After completion of the reaction, samples were taken out from the reaction mixture, and they were subjected to LC analysis. As a result, it was found that the mixture contained 2.7% of the starting material, 91.2% of the monobromo-product, and 5.4% of the dibromo-product. Accordingly, the selectivity of the monobromo-product over the dibromo-product was 94.4%.

Thereafter, the purification treatment as in Example 1 was carried out, to give 61.8 g of 4'-bromomethyl-2-cyanobiphenyl with an LC purity of 98.6%. The yield was 87.7%, based on the starting material.

Example 5

The same procedures as in Example 1 were carried out except that 500 g of n-heptane was used in place of ethylene dichloride. After completion of the reaction, samples were taken out from the reaction mixture, and they were subjected to LC analysis. As a result, it was found that the mixture contained 2.9% of the starting material, 90.6% of the monobromo-product, and 5.8% of the dibromo-product. Accordingly, the selectivity of the monobromo-product over the dibromo-product was 94.0%.

Thereafter, the purification treatment as in Example 1 was carried out, to give 60.9 g of 4'-bromomethyl-2-cyanobiphenyl with an LC purity of 98.5%. The yield was 86.4%, based on the starting material.

Comparative Example 1

Fifty grams (0.2591 mol) of 4'-methyl-2-cyanobiphenyl, 500 g of ethylene dichloride, and 4.0 g (0.0130 mol) g of 2,2'-azobis(4-methoxy-2,4-dimethylvaleronitrile) were placed in a reaction vessel, and the internal temperature was controlled to 40°±2° C. Thereafter, 46.1 g (0.2590 mol) of N-bromosuccinimide was added dropwise at the same temperature over a period of 2 hours, and then the reaction mixture was kept at that temperature for one hour. At this point of reaction, samples were taken out from the reaction mixture, and they were subjected to LC analysis. As a result, it was found that the mixture contained 2.0% of the starting material, 86.3% of the monobromo-product, and 9.6% of the dibromo-product. Accordingly, the selectivity of the monobromo-product over the dibromo-product was 90.0%.

Thereafter, the reaction mixture was washed with 250 g of water, and then the mixture was separated to two layers. The organic layer was condensed by removing the solvent. The obtained solid was recrystallized from ethylene dichloride (150 ml)-n-heptane (600 ml), to give 56.1 g of 4'-bromomethyl-2-cyanobiphenyl with an LC purity of 97.8%. The yield was 79.6%, based on the starting material.

Comparative Example 2

The same procedures as in Comparative Example 1 were carried out except that 2.1 g (0.0128 mol) of 2,2'-azobisisobutyronitrile was used in place of 2,2'-azobis(4-methoxy-2,4-dimethylvaleronitrile), and the reaction temperature was changed to 70° C. After completion of the reaction, samples were taken out from the reaction mixture, and they were subjected to LC analysis. As a result, it was found that the mixture contained 8.7% of the starting material, 80.2% of the monobromo-product, and 9.2% of the dibromo-product. Accordingly, the selectivity of the monobromo-product over the dibromo-product was 89.7%.

Thereafter, the purification treatment as in Comparative Example 1 was carried out, to give 52.5 g of 4'-bromomethyl-2-cyanobiphenyl with an LC purity of 97.7%. The yield was 74.5%, based on the starting material.

As is clear from the above results, Examples of the present invention had a higher yield by about 10% while maintaining the monobromo-product selectivity to a level equivalent or higher than those of Comparative Examples where conventionally used halogenation agents were used.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing 4'-bromomethyl-2-cyanobiphenyl represented by formula (II):

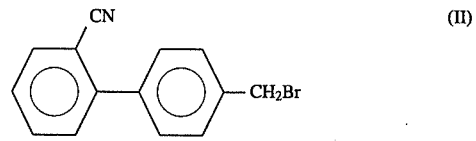

comprising a step of treating 4'-methyl-2-cyanobiphenyl represented by formula (I):

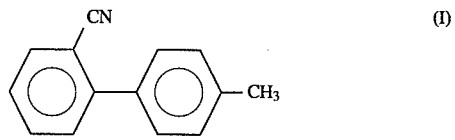

with $Br_2$ in a halogenated hydrocarbon solvent or an alkane solvent having 5 to 7 carbon atoms wherein the step is carried out in the presence of a radical initiator, wherein said radical initiator is selected from the group consisting of 2,2'-azobis(4-methoxy-2,4-dimethylvaleronitrile), 2,2'-azobisisobutyronitrile, and dibenzoyl peroxide.

2. The method according to claim 1, wherein said $Br_2$ is used in an amount of from 0.8 to 1.5 times by mol, based on said 4'-methyl-2-cyanobiphenyl.

3. The method according to claim 1, wherein said solvent is selected from the group consisting of methylene chloride, ethylene dichloride, carbon tetrachloride, monochlorobenzene, o-dichlorobenzene, bromobenzene, hexane, heptane, and cyclohexane.

4. The method according to claim 1, wherein an amount of the solvent used is from 1 to 20 times the weight of said 4'-methyl-2-cyanobiphenyl.

5. The method according to claim 1, wherein an amount of said radical initiator used is from 0.1 to 10 mol %, based on said 4'-methyl-2-cyanobiphenyl.

6. The method according to claim 1, wherein a reaction temperature is from 0° to 100° C.

* * * * *